US007259344B2

(12) United States Patent
Zhang et al.

(10) Patent No.: US 7,259,344 B2
(45) Date of Patent: Aug. 21, 2007

(54) APPLICATION OF STATIC LIGHT TO A FLUID OF CNTS FOR PURPOSES OF SORTING THE CNTS

(75) Inventors: Yuegang Zhang, Cupertino, CA (US); Herman A. Lopez, San Joe, CA (US); Shida Tan, Milpitas, CA (US)

(73) Assignee: Intel Corporation, Santa Clara, CA (US)

( * ) Notice: Subject to any disclaimer, the term of this patent is extended or adjusted under 35 U.S.C. 154(b) by 202 days.

(21) Appl. No.: 10/956,597

(22) Filed: Oct. 1, 2004

(65) Prior Publication Data

US 2006/0070920 A1   Apr. 6, 2006

(51) Int. Cl.
*B03C 7/00*     (2006.01)

(52) U.S. Cl. ........................ 209/128; 209/210; 977/845

(58) Field of Classification Search ................ 209/129, 209/130, 156, 210, 128; 977/845
See application file for complete search history.

(56) References Cited

U.S. PATENT DOCUMENTS

| 6,974,926 B2 * | 12/2005 | Zhang et al. ................ 209/129 |
| 2003/0183560 A1 | 10/2003 | Hannah |
| 2004/0084353 A1 | 5/2004 | Hannah |
| 2004/0120880 A1 | 6/2004 | Zhang et al. |
| 2005/0122550 A1 * | 6/2005 | Plewa et al. ................... 359/10 |

* cited by examiner

*Primary Examiner*—Joseph C. Rodriguez
(74) *Attorney, Agent, or Firm*—Blakely, Sokoloff, Taylor & Zafman LLP

(57) ABSTRACT

A method is described that comprises sorting carbon nanotubes (CNTs) within a fluidic flow for a targeted subset of the CNTs. The sorting comprises attracting at least a portion of the CNTs within the fluidic flow in a direction of increasing intensity of an electric field component of a substantially stationary beam of light. The electric field component has a frequency that is less than one or more resonant frequencies of the CNTs within the portion.

12 Claims, 10 Drawing Sheets

APPLICATION OF STATIC LIGHT TO A FLUID OF CNTS FOR PURPOSES OF SORTING THE CNTS

FIELD OF INVENTION

The field of invention relates generally to carbon nanotubes (CNTs); and, more specifically, to the application of static light to a fluid flow of CNTs for purposes of sorting the CNTs.

BACKGROUND

Carbon nanotubes (CNTs) can be viewed as a sheet of Carbon that has been rolled into the shape of a tube (end capped or non-end capped). CNTs having certain properties (e.g., a "conductive" CNT having electronic properties akin to a metal) may be appropriate for certain applications while CNTs having certain other properties (e.g., a "semiconducting" CNT having electronic properties akin to a semiconductor) may be appropriate for certain other applications. CNT properties tend to be a function of the CNT's "chirality" and diameter. The chirality of a CNT characterizes its arrangement of carbon atoms (e.g., arm chair, zigzag, helical/chiral). The diameter of a CNT is the span across a cross section of the tube.

Because the properties of a CNT can be a function of the CNT's chirality and diameter, the suitably of a particular CNT for a particular application is apt to depend on the chirality and diameter of the CNT. Unfortunately, current CNT manufacturing processes are only capable of manufacturing batches of CNTs whose tube diameters and chiralities are widely varied. The problem therefore arises of not being able to collect CNTs (e.g., for a particular application) whose diameter and chiralities reside only within a narrow range (or ranges of) those that have been manufactured.

United States Patent Application Publication U.S. 2004/0120880 by Zhang, Hannah and Woo (hereinafter "Zhang et al.") and entitled "Sorting of Single-Walled Carbon Nanotubes Using Optical Dipole Traps" teaches that CNTs of specific chirality and diameter will posses electrical dipole moments that will cause the CNT to exhibit characteristic "attraction/repulsion" behavior under an applied time-varying electric field. As such, Zhang et al further teaches a technique that uses the characteristic "attraction/repulsion" behavior as a basis for collecting "targeted" CNTs of specific tube chirality and diameter.

With respect to a CNT's "attraction/repulsion" behavior, Zhang et al. teaches that the system energy of a CNT placed in a time-varying electric field is $U=-\frac{1}{2}\epsilon_0 \chi E^2$ where $\epsilon_0$ is the permitivity of free space, $\chi$ is the dielectric susceptibility of the CNT and $E^2$ is the intensity of the time-varying electric field. The dielectric susceptibility $\chi$ describes the collective orientation and strength of the individual electric dipole moments of the CNT in response to the applied time-varying electric field. According to Zhang et al., the dielectric susceptibility $\chi$ is a function of the frequency of the applied electric field; and, more importantly, that the collective "direction" of the CNT's electric dipole moments change as a function of frequency.

Specifically, for applied electric field frequencies beneath a "resonant" frequency, the dipole moments collectively "point" in a direction that causes the CNT to move towards increasing electric field intensity (i.e., the CNT is attracted to regions of increasing electric field intensity because lower system energy results from higher electric field intensities); while, for applied electric field frequencies above the aforementioned resonant frequency, the dipole moments collectively "point" in a direction that causes the CNT to move away from increasing electric field intensity (i.e., the CNT is repelled from regions of increasing electric field intensity because higher system energy results from higher electric field intensities). If the frequency of the applied time-varying electric field is at the resonant frequency, the collective pointing direction and motion of the CNT is unstable.

Zhang et al also teaches that the specific resonant frequencies of a CNT are a function of its energy bandgaps, and that, the energy bandgaps of a CNT are a function of the CNT's chirality and diameter. Hence, the aforementioned characteristic attraction/repulsion behavior of a CNT in response to an applied time-varying electric field is a function of the CNT's chirality and diameter.

Zhang et al. further describes a technique for sorting CNTs based upon the above described attraction/repulsion behavior. In particular, if an electric field is applied to a group of CNTs having diverse chiralities and diameters (e.g., such as a batch of CNTs produced by a single manufacturing process run), a specific CNT can be collected through the application of a time-varying electric field whose frequency is tailored in light of the resonant frequency of the CNT sought to be collected. FIGS. 1a through 1c demonstrate the technique in more detail.

FIG. 1a shows a fluidic flow 103 containing manufactured CNTs. It is assumed that the manufactured CNTs have various combinations of diameter and chirality. For simplicity, FIG. 1a shows only two types of manufactured CNTs: 1) a first group 105, 107, 110, 111, 112, 114, 117, 119 having a first chirality and diameter combination; and, 2) a second group 106, 108, 109 113, 115, 116, 118, 120 having a second chirality and diameter combination. All of the CNTs 105 through 120 enter the apparatus as part of fluidic flow $103_1$. A second fluidic flow 104 flows along side fluidic flow 103.

The general idea is that a particular type of CNT, such as the CNTs associated with the first group defined above, is to be extracted from fluidic flow 103 and introduced to fluidic flow 104. Thus, CNTs of the first type will flow out of the apparatus as part of fluid flow $104_2$ and CNTs of the second type will flow out of the apparatus as part of fluid flow $103_2$.

The extraction process uses the electric field component of a laser beam to apply the time-varying electric field. A laser beam spot 101 is drawn as being impingent upon fluid flow 103. The laser beam is focused and thus converges to a source image 102 further along the x axis approximately within the center of fluid flow 103's cross section (FIG. 2, which is discussed in more detail ahead, provides a three dimensional perspective of a laser beam focused as just described).

A focused point 102 in the center of the fluid flow causes the electric field intensity of any region that is illuminated by the laser beam to increase in the direction toward the focused point 102. Therefore, by selecting a laser beam frequency that is beneath the resonant frequency of the first group of CNTs but above the resonant frequency of the second group of CNTs, CNTs from the first group will be attracted toward the focused point 102 while CNTs from the second group will be repelled from the focused point 102.

At the instant of time represented by FIG. 1a, sweeping the laser beam from fluid flow 103 to fluid flow 104 will cause CNTs 105 and 107 to be pulled, as a consequence of their attraction to focused point 102, into fluid flow 104; while, CNT 106, as a consequence of its repulsion from point 102, will remain in fluid flow 103. The situation after the sweeping of the laser beam is depicted in FIG. 1b.

It is clear from the situation of FIG. 1b that CNTs 105 and 107 will exit as part of exit flow 104₂ and that CNT 106 will exit as part of exit flow 103₂. FIG. 1c shows the situation if the laser beam is swept again from flow 103 to 104 so as to capture CNTs 110, 111 and 112 from flow 103 and introduce them to flow 104. It is also clear that repeating this sweeping motion will cause the CNTs of the first group to exit as part of exit flow 104₂ and that CNTs of the second group will exit as part of exit flow 103₂. Thus, the sorting of CNTs is accomplished.

FIGURES

The present invention is illustrated by way of example, and not limitation, in the figures of the accompanying drawings in which like references indicate similar elements and in which.

DESCRIPTION

Figure 1A:
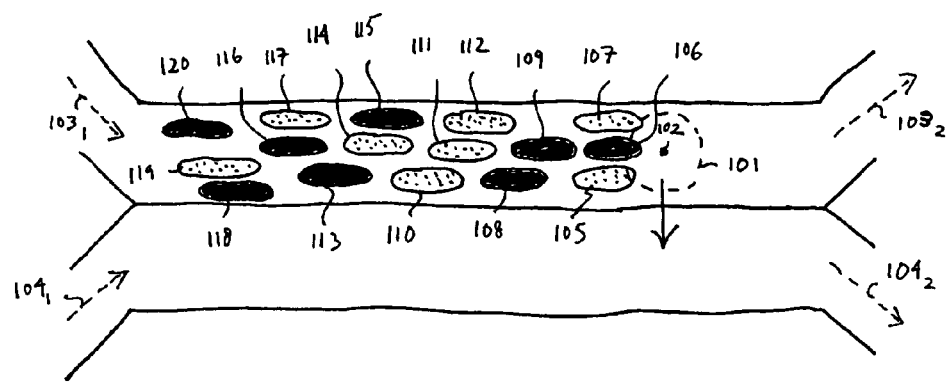
FIG. 1 (prior art) shows a technique for sorting CNTs that employs the sweeping of a laser beam.
Figure 1B:
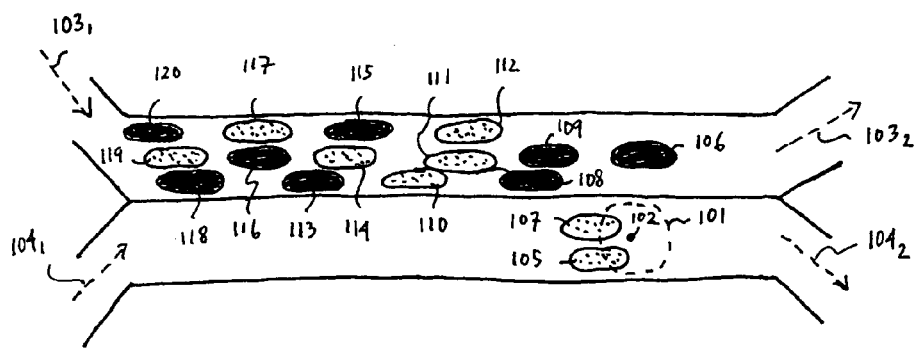
Figure 1C:
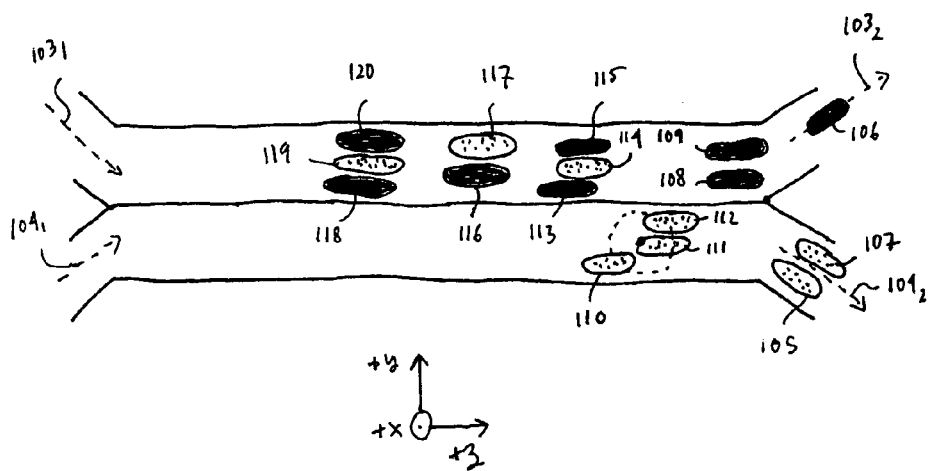
Figure 2:
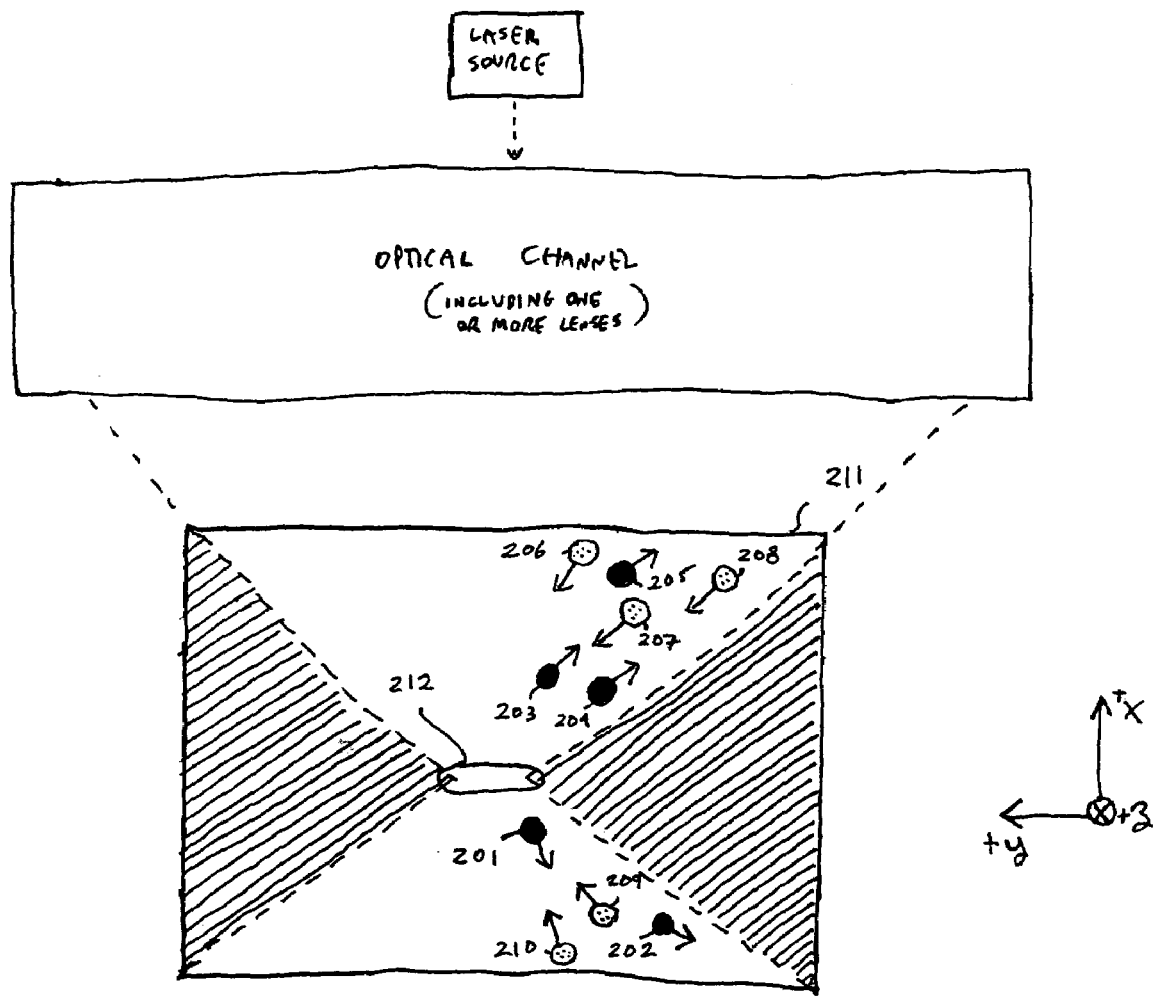
FIG. 2 shows attraction/repulsion behavior of CNTs of diverse chirality and diameter in response to the electric field component of a focused laser beam within a fluidic flow containing the CNTs.

FIG. 2 provides a three dimensional perspective of the attraction/repulsion behavior of CNTs within a fluidic flow in response to the electric field component of a focused laser beam. Here, FIG. 2 is drawn from the perspective of a cross section of the fluid flow. That is, FIG. 2 is consistent with FIG. 1 in that the fluidic flow is assumed to be in the +z direction. The cross section 211 of the fluid flow is assumed to be rectangular. The region of the fluidic flow that is illuminated by light from the focused laser beam light is drawn as not being shaded; and, the region of the fluidic flow that is not illuminated by the light from the focused laser beam is drawn as being shaded.

The laser beam light is focused 212 in approximately the middle of the fluidic flow so as to establish a gradient in electric field intensity throughout the illuminated region. Specifically, within the illuminated region, the electric field intensity increases in any direction toward the focused spot 212. Here, unlike FIG. 1, note that the CNTs 201 through 210 in the fluidic flow of FIG. 2 are depicted as being concentrated on one side of the fluidic flow (i.e., the right hand side).

Vectors are drawn from each of the CNTs 201-210 in FIG. 2 to demonstrate the direction of the induced motion that each CNT will experience under the influence of the electric field component of the laser beam. Here, CNTs 201, 202, 203, 204, 205 are like the "second group" discussed above with respect to FIG. 1 in that each of these CNTs is repelled from focused spot 212. Also, CNTs 206, 207, 208, 209, 210 are like the "first group" discussed above with respect to FIG. 1 in that each of these CNTs is attracted to focused spot 212. The vector arrangement observed in FIG. 2 can be configured, for instance, if the frequency of the laser light is less than the resonant frequency of the first group CNTs but higher than the second group CNTs.

Importantly, because the CNTs 201-210 are concentrated on the right hand side of focused spot 212, the vector of every CNT from the second group has a component directed along the −y axis; and, the vector of every CNT from the first group has a component directed along the +y axis. As such, all CNTs from the second group will exhibit some degree of momentum/motion in the −y direction and all CNTs from the first group will exhibit some degree of momentum/motion in the +y direction.

As such, a sorting mechanism is made to exist. That is, collectively, the first group CNTs are moving in a direction opposite that of the second group CNTs. Given enough time, without any collisions, the CNTs from the different groups will completely separate from one another even if the laser beam light is removed (i.e., conservation of momentum acts to allow the CNTs to continue to travel along the vectors indicated). This new separation technique just described above, unlike the technique discussed above with respect to FIG. 1, does not need to sweep the laser beam. That is, the laser beam can remain substantially fixed ("static") in terms of its position within the fluidic flow. Thus, at least with respect to the optics, the new technique of FIG. 2 should be less complicated than the technique of FIG. 1.

Figure 3:
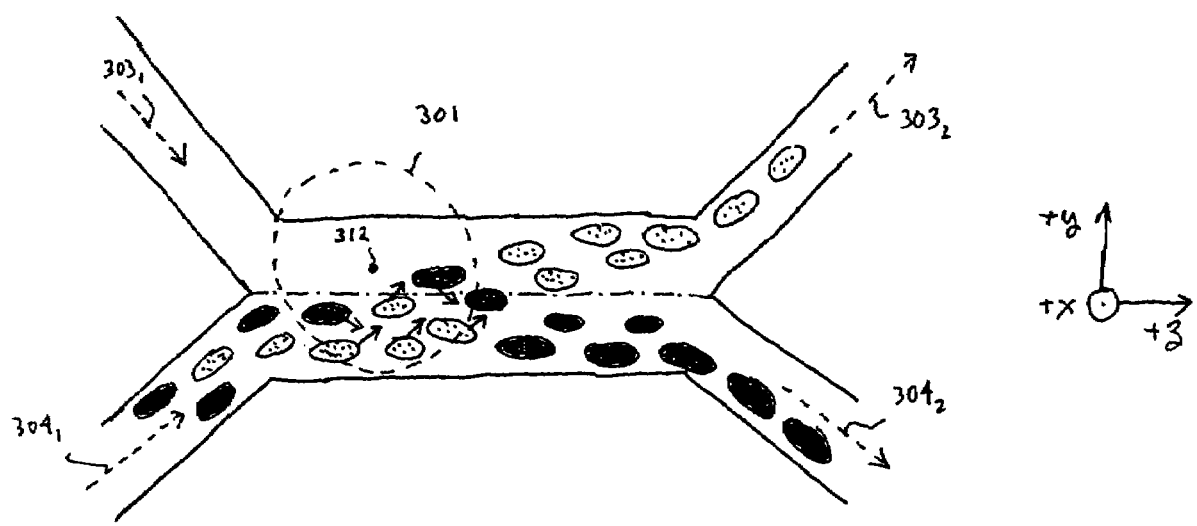
FIG. 3 shows a technique that employs a stationary laser beam to sort CNTs within a fluidic flow.

In order to effect the separation mechanism of FIG. 2, as mentioned above, the CNTs should be concentrated toward the side of the focused laser beam spot 212. FIG. 3 depicts an apparatus configured to influence the flow of CNTs along a side of a focused laser beam spot 312 so as to effect the sorting technique described just above. According to the apparatus of FIG. 3, two fluidic flows 303, 304 are made to run along side one another in the +z direction. CNTs are introduced along the input flow of fluidic flow 304 (i.e., fluidic flow 304₁). The basic strategy is to attract "targeted" CNTs of specific chirality and diameter (or range thereof) from fluidic flow 304 to fluidic flow 303.

The laser beam light is configured to effect the attraction of the targeted CNTs. In particular, because only those CNTs that are illuminated by the light are affected by the sorting technique, the diameter of the laser beam light 301 is made expansive so as to illuminate as many CNTs from fluidic flow 304₁ as is possible. Here, one technique for focusing laser beam light from an expansive beam is to focus the light from a large numerical aperture (NA) lens (e.g., an NA between 0.5 and 1.5 inclusive). Moreover, the focused spot 312 is placed within fluidic flow 303 (or at the border of fluidic flow 303 and 304) and proximate to the convergence of input flows 303₁ and 304₁ so as to ensure that targeted CNTs are not repelled from fluidic flow 303. Lastly, the laser beam's electric field component has a frequency that is less than the resonant frequency of the targeted CNTs.

FIG. 3 shows exemplary motion vectors for those CNTs that are illuminated by the laser beam light 301. All of the observed motion vectors have a component in the +z direction at least because of the fludic flow. Moreover, the targeted CNTs have a motion component in the +y direction toward fluidic flow 303; and, the non targeted CNTs have a motion component in the −y direction away from fluidic flow 303. As a consequence of their +y motion components, the targeted CNTs will drift into fluidic flow 303 even after they flow downstream past the laser light 301 (i.e., conservation of momentum acts to cause the targeted CNTs to continue traveling in the +y direction even after they are no longer irradiated with a time varying electric field). Likewise, as a consequence of their −y motion components, the non-targeted CNTs will drift away from fluidic flow 303 even after they flow downstream past the laser light 301 (i.e., conservation of momentum acts to cause the non targeted CNTs to continue traveling in the −y direction even after they are no longer irradiated with a time varying electric field). As such, by the time the fluidic flows reach their exit regions, the targeted CNTs will be carried by exit flow $303_2$ and the non-targeted CNTs will be carried by exit flow $304_2$.

Figure 4:
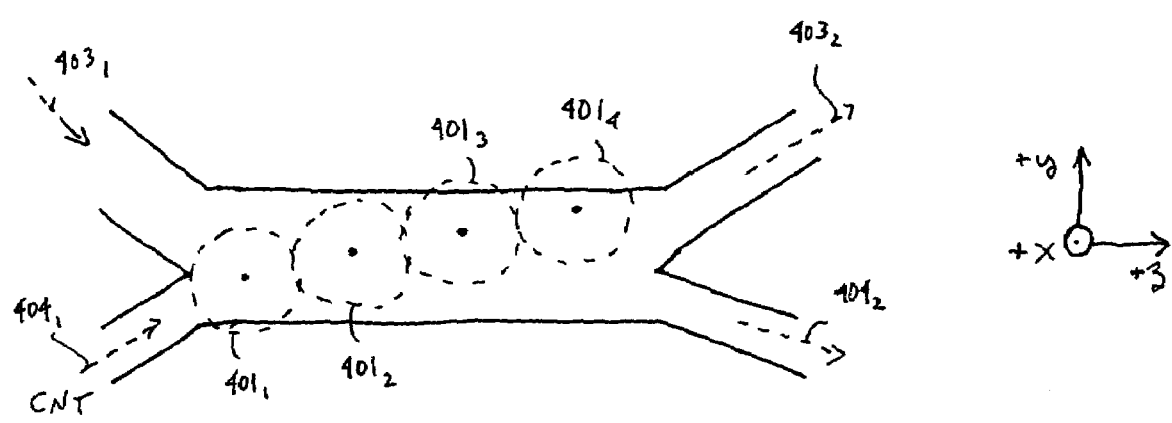
FIG. 4 shows an expansion of the technique of FIG. 3 in which a plurality of stationary laser beams are used to sort CNTs within a fluidic flow.

FIG. 4 shows an improvement over the basic apparatus of FIG. 3. According to the approach of FIG. 4, a plurality of laser beams $401_1$ through $401_4$ are used to attract the targeted CNTs. Here, although four separate laser beams are shown, it should be understood that more or less than four laser beams may be used depending on design. Like the approach of FIG. 3, a pair of fluid flows 403, 404 are made to run along side one another. CNTs enter the apparatus as part of entry flow $404_1$.

The plurality of laser beams $401_1$-$401_4$ effectively set up a wall of light that continually attracts targeted CNTs toward fluid flow 403 and continually repels non targeted CNTs away from fluid flow 403 as the CNTs flow for an extended distance downstream (e.g., according to one embodiment, the electric field component of each laser beam has a frequency that is less than the resonant frequency of the targeted CNTs). Like the approach of FIG. 3, targeted CNTs should emerge from exit flow $403_2$ and non targeted CNTs should emerge from exit flow $404_2$. Of course, a series of lenses could be used to form the wall of light.

In the embodiment of FIG. 4, the "wall" of laser beams are oriented such that the wall gradually recedes further and further in the +y direction into fluidic flow 403. The effect of orienting the wall in this manner is to begin to attract targeted CNTs in the proximity of the first beam $401_1$ and then "hand off" the targeted CNTs to the attractive forces of the second beam $401_2$. As the targeted CNTs move downstream they are next "handed off" to the attractive forces of the third beam $401_3$. By the time the targeted CNTs have moved sufficiently downstream to be handed off to the attractive forces of the fourth beam $401_4$, they are well within fluidic flow 403 and therefore should exit the apparatus from exit flow $403_2$.

By contrast, any non targeted CNTs that reside within fluidic flow 403 should be repelled by the wall of light. In the embodiment of FIG. 4, the last beam $401_4$ is sufficiently distant from exit flow $404_2$ so as to allow any non targeted CNT that is provided momentum toward fluidic flow 404 by the repelling forces of beam $401_4$ enough time to drift into fluidic flow 404.

In a further embodiment, the focused spots of the laser beams $401_1$ through $401_4$ are positioned at different levels along the x axis so as to more fully illuminate the fluidic flows through the apparatus. As a consequence, the collection efficiency of targeted CNTs should be more efficient than the approach of FIG. 3. In order to understand the concept in more detail, referring to FIG. 2, note that the motion of targeted and non targeted CNTs alike will not be affected for those CNTs that pass only through the non illuminated shaded region. By having multiple beams whose focused spots are positioned at different levels along the x axis, fewer targeted CNTs should be able to "miss" the illuminated regions of fluidic flow.

In an alternative embodiment, in order to even further enhance the collection efficiency of the targeted CNTs, the wall of laser beams not only include different x axis locations for its respective focused spots, but also, the wall is not made to recede gradually into fluidic flow 403 and instead runs in the +z direction (i.e., substantially along the direction of the fluidic flow). So orienting the wall of laser beams creates an even greater likelihood that all CNTs will flow through the illuminate region of at least one laser beam.

Figure 5:
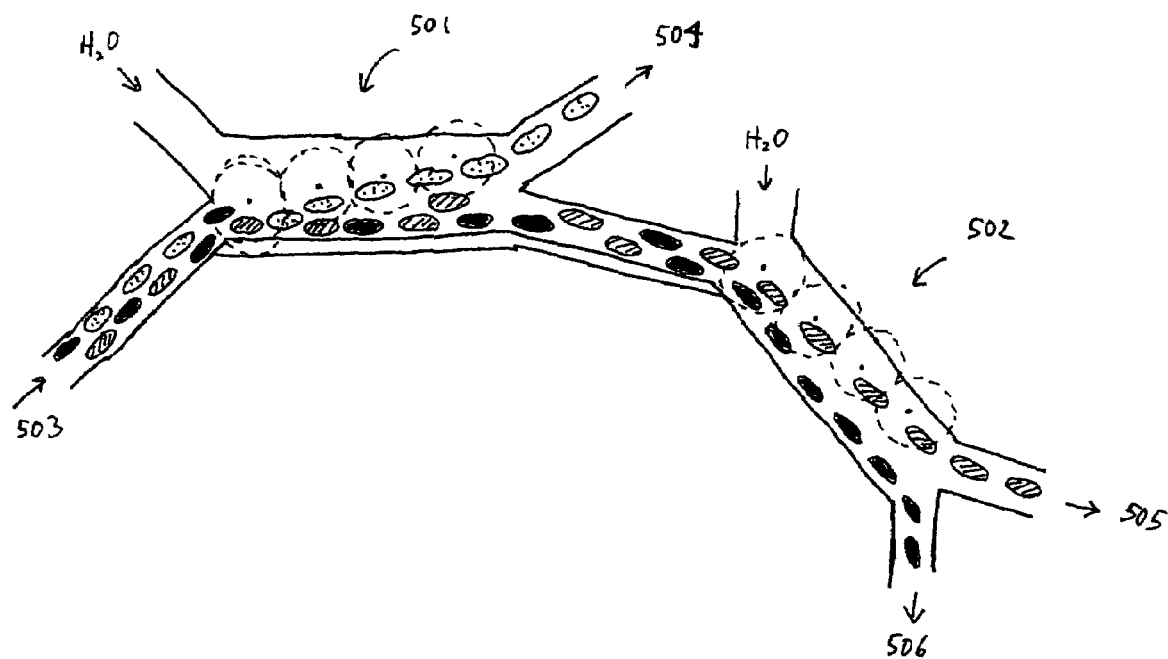
FIG. 5 shows a cascaded sorting apparatus for sorting multiple types of CNTs within a fluid flow.

FIG. 5 shows another embodiment is which of pair of sorters like that in FIG. 4 are coupled in a cascaded fashion so as to sort multiple types of CNTs. In particular, the sorter apparatus of FIG. 5 is meant to sort three different kinds of CNTs: "dotted", "shaded" and "darkened". The first wall 501 is constructed of light whose frequency is less than that of the resonant frequency of the "dotted" CNTs but greater than that of the "shaded" and "darkened" CNTs. The second wall 502 is constructed of light whose frequency is less than the resonant frequency of the "shaded" CNTs but greater than the resonant frequency of the "darkened" CNTs.

CNTs are entered at entry flow 503. From the arrangement described above, the first wall 501 will attract "dotted" CNTs such that they flow from exit flow 504 and will repel the "shaded" and "darkened" CNTs into the flow that flows to wall 502. The second wall 502 will attract "shaded" CNTs such that they flow from exit flow 505 and will repel "darkened" CNTs such that they flow from exit flow 506. In an embodiment, the "dotted" CNTs have the lowest resonant frequency amongst all the CNTs and the "shaded" CNTs have the second lowest resonant frequency amongst all the CNTs. So doing guarantees that any missed "dotted" CNTs targeted by wall 501 will be repelled by wall 502 so as not to taint output flow 505 with "dotted" CNTs.

In order to enhance the collection efficiency of any of the sorting techniques observed in FIGS. 3, 4 and 5, the fluid flow that is not fed by a attractive force may be fed back to the input flow. For example, referring to FIG. 3, exit flow $304_2$ may be fed back to input flow $304_1$; referring to FIG. 4, exit flow $404_2$ may be fed back to input flow $404_1$; and, referring to FIG. 5, exit flow 506 may be fed back to input flow 503. Here, it is assumed that all targeted CNTs may not be caught by the attractive forces of the light beam(s) that have been configured to capture them. As such, there is some probability that targeted CNTs will not flow out the desired exit port the first time they pass by the light.

In the case of FIGS. 3 and 4, coupling flow $304_2$ back to flow $304_1$ and flow $404_2$ back to flow $404_1$ allows those targeted CNTs that were not captured (i.e., "missed") along a pass by of the laser light to have another chance at being captured. Moreover, in the case of FIG. 5, coupling flow 506 back to flow 503, permits "dotted" CNTs that were not captured along a pass-by of wall 501 to be recaptured. Here, as described above, any missed "dotted" CNTs will be repelled by wall 502 provided that the "dotted" CNTs have lower resonant frequency than the "shaded" CNTs.

As another approach, to increase the total flow of targeted CNTs per cycle, the cascade structure of FIG. 5 may be used where the electric field component frequency of both walls 501, 502 is the same (or, at least, the electric field component frequencies of both walls 501, 502 are tailored to attract the same CNTs). According to this approach, should any targeted CNTs "miss" wall 501, they may be attracted by wall 502 so as to flow from output flow 505. Additional stages may be added to further increase the sorting efficiency.

Figure 6:
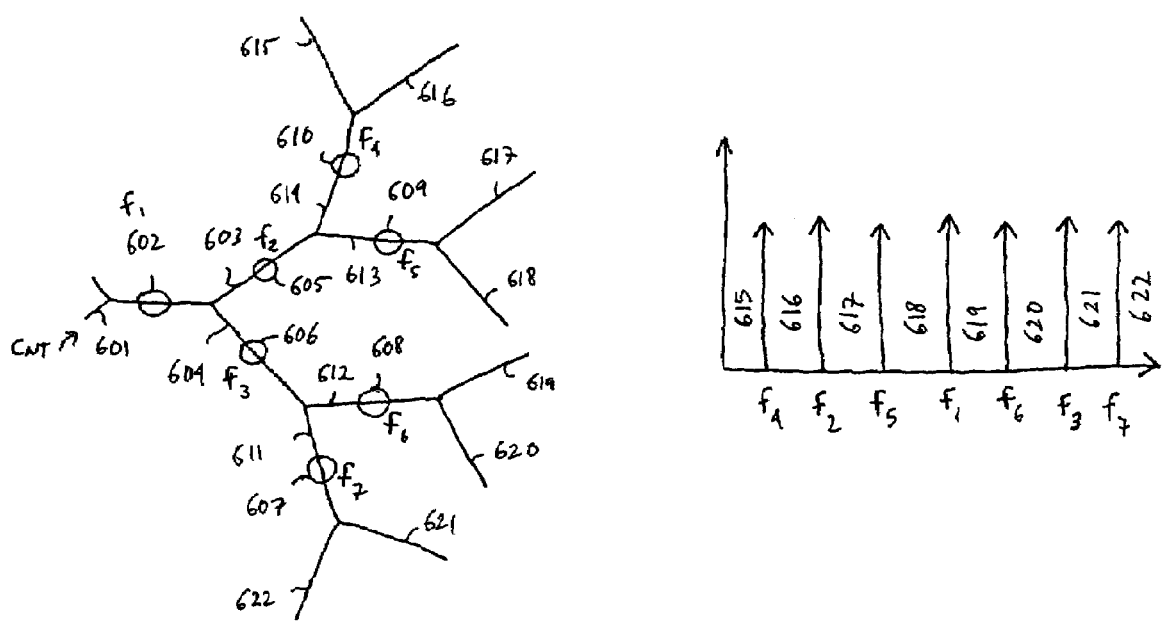
FIG. 6 shows an expanded version of the cascade sorting apparatus of FIG. 5.

FIG. 6 shows a multi-dimensional expansion of the sorting strategy of FIG. 5 in which the electric field intensity of various applied laser beams are configured to provide multiple output flows for different types of targeted CNTs. According to the technique of FIG. 6, a batch of manufactured CNTs are entered at input flow 601 and the electric field component frequency f1 of a first laser beam 602 (wall or otherwise) divides (e.g., approximately "in half") the anticipated range of manufactured chirality and diameter combinations such that those CNTs having a resonant frequency beneath f1 are attracted to fluidic flow leg 603 and that those CNTs having a resonant frequency above f1 are repelled to fluidic flow leg 604.

The electric field component frequency f2 of a second laser beam 605 (wall or otherwise, where f2 is less than f1) divides (e.g., approximately "in half") those CNTs that flow through leg 603 such that those CNTs having a resonant frequency beneath f1 and f2 are attracted to fluidic flow leg 614 and those CNTs having a resonant frequency beneath f1 and above f2 are repelled to fluidic flow leg 613. The electric field component frequency f3 of a third laser beam 606 (wall or otherwise, where f3 is greater than f1) divides (e.g., approximately "in half") those CNTs that flow through leg 604 such that those CNTs having a resonant frequency above f1 and beneath f3 are attracted to fluidic flow leg 612 and those CNTs having a resonant frequency above f1 and above f3 are repelled to fluidic flow leg 611.

The electric field component frequency f4 of a fourth laser beam 610 (wall or otherwise, where f4 is less than f2) divides (e.g., approximately "in half") those CNTs that flow through leg 614 such that those CNTs having a resonant frequency beneath f1, f2 and f4 are attracted to fluidic flow leg 615 and those CNTs having a resonant frequency beneath f1 and f2 and above f4 are repelled to fluidic flow leg 616. The electric field component frequency f5 of a fifth laser beam 609 (wall or otherwise, where f5 is greater than f2 but less than f1) divides (e.g., approximately "in half") those CNTs that flow through leg 613 such that those CNTs having a resonant frequency beneath f1, above f2 and beneath f5 are attracted to fluidic flow leg 617 and those CNTs having a resonant frequency beneath f1, above f2 and above f5 are repelled to fluidic flow leg 618.

The electric field component frequency f6 of a sixth laser beam 608 (wall or otherwise, where f6 is less than f3 but greater than f1) divides (e.g., approximately "in half") those CNTs that flow through leg 612 such that those CNTs having a resonant frequency above f1, beneath f3 and below f6 are attracted to fluidic flow leg 619 and those CNTs having a resonant frequency above f1 beneath f3 and above f6 are repelled to fluidic flow leg 620. The electric field component frequency f7 of a seventh laser beam 607 (wall or otherwise, where f7 is greater than f1 and f3) divides (e.g., approximately "in half") those CNTs that flow through leg 611 such that those CNTs having a resonant frequency above f1, above f3 and beneath f7 are attracted to fluidic flow leg 621 and those CNTs having a resonant frequency above f1, above f3 and above f7 are repelled to fluidic flow leg 622.

Figure 7:
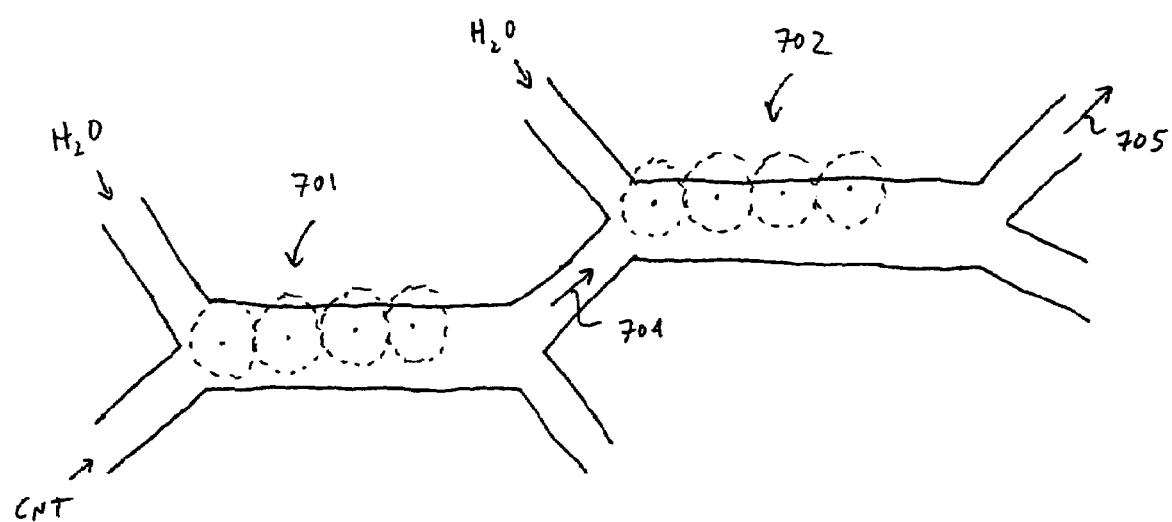
FIG. 7 shows a sorting apparatus for producing purified concentrations of targeted CNTs.

FIG. 7 shows another approach that may be used to produce high purity concentrations of targeted CNTs (i.e., the collection of CNTs outside the targeted range is diminished). FIG. 7 is comparable to FIG. 5 except that an output fluid channel 705 exists that is fed by two or more laser beam walls 701, 702 that attract the targeted CNTs. That is, laser beam wall 701 attracts targeted CNTs into fluidic flow 704; and, laser beam wall 702 attracts targeted CNTs into fluidic flow 705. As such, in order for a non targeted CNT to exit from fluidic flow 705, it will have to escape the repelling forces of both of walls 701 and 702. Additional one or more laser beam wall stages designed to attract targeted CNTs can be designed to follow from fluidic flow 705 so as to further enhance the purity of the ultimate output flow.

In the above descriptions, the electric component frequency of the applied laser light has always been suggested to be less than the resonant frequency of the "targeted" CNTs. In reverse embodiments, rather than attempt to attract targeted CNTs as described above, the electric field component frequency is set to be greater than a targeted CNT's resonance (so as to repel the targeted CNT) but less than one or more non targeted CNTs (so as to attract the non targeted CNTs). In this case, for example, referring to FIGS. 3, 4 and 5, the targeted CNTs emanate from flows $304_2$, $404_2$, and 506, respectively.

Figure 8A:
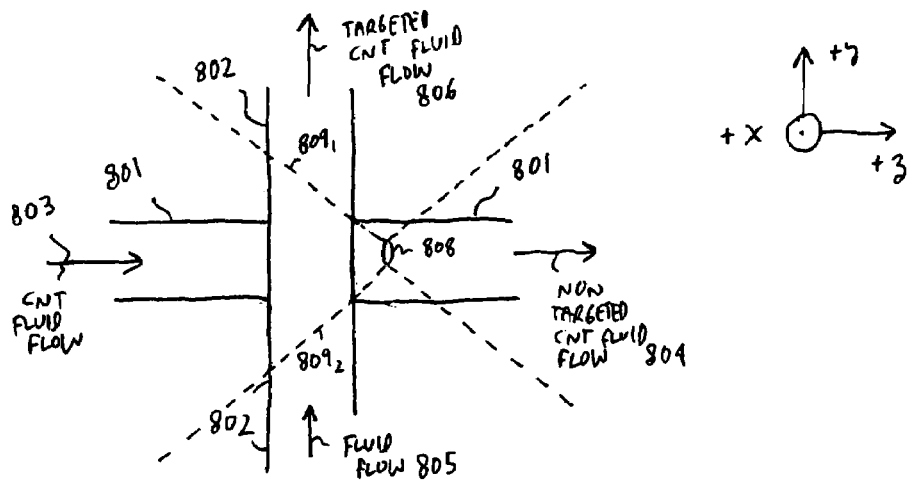
FIGS. 8a through 8f show CNT sorting where collected CNTs flow along a different vertical plane than the plane along which CNTs to be sorted flow.
Figure 8B:
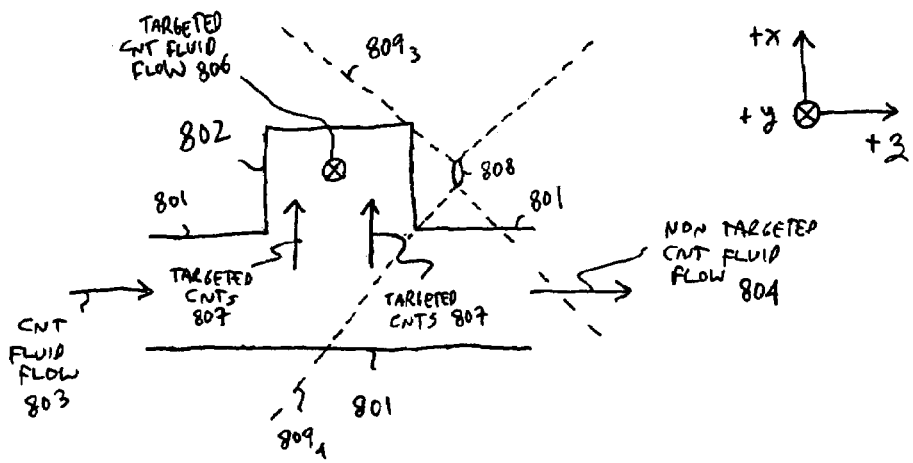
Figure 8C:
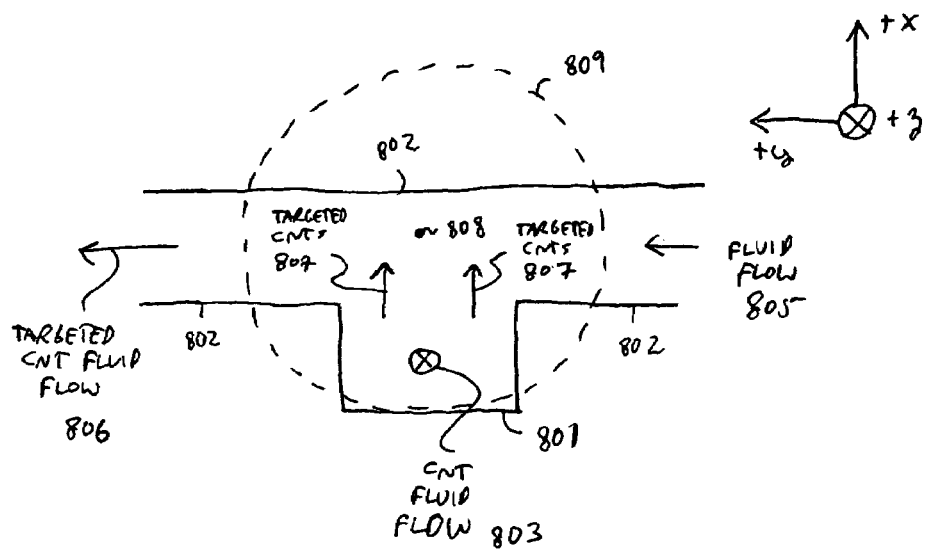

FIGS. 8a-8c shows another embodiment of a sorting technique using stationary laser light where collected CNTs flow along a different vertical plane than the flow of CNTs to be sorted 803. According to the approach of FIGS. 8a-8c, a flow of CNTs to be sorted 803 flows along a first flow channel 801 that runs "beneath" (when measured along the x axis) a second fluid channel 802 that is designed to collect targeted CNTs within the flow of CNTs to be sorted 803. The fluid flow of the second channel 802 runs in the +y direction. As such, pure fluid 805 flows in channel 802 before the intersection of channels 801 and 802; and, a fluid flow of collected, targeted CNTs 806 flows after the intersection of channels 801 and 802.

Laser beam light is shaped and given the appropriate electric field component frequency to attract targeted CNTs from flow 803 "up" into channel 802. According to the observed depiction, a focused spot of the laser light 808 is positioned such that: 1) the laser's light 809 illuminates the intersection region of the two channels; and, 2) the flow of CNTs to be sorted 803 run along a side of the circular/elliptical shape of the light 809 similar to that described with respect to FIG. 2 (in particular, as observed, flow 803 runs through a "lower" portion of the circular/elliptical field of light 809. Moreover, the frequency of the electric field component of the light is made to have a frequency that is less than the resonant frequency of the targeted CNTs.

These conditions will cause an increasing electric field intensity gradient to be established in the region of intersection of the two channels so that: 1) targeted CNTs will be pulled "up" in the +x direction 807 from channel 801 into channel 802; and, 2) non targeted CNTs (or at least those CNTs having a resonant frequency above the laser beam's electric field component frequency) will be repelled further "downward" in channel 802 in the −x direction. As such targeted CNTs exit at flow 806 and non targeted CNTs exit at flow 804.

In an alternate embodiment, the laser beam spot 808 could be lowered directly from its depicted position beneath channel 801 and the frequency of the electric field component of the light could be raised above the resonant frequency of the targeted CNTs but beneath the resonant frequency of all other CNTs. This approach would "repel" the targeted CNTs "up" into channel 802 and would attract all other CNTs to remain in channel 801.

Figure 8D:
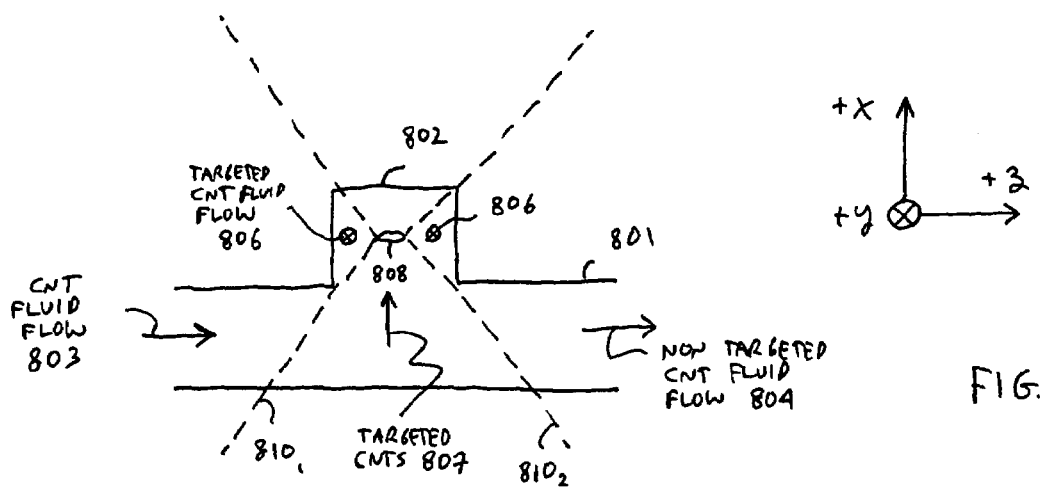
Figure 8E:
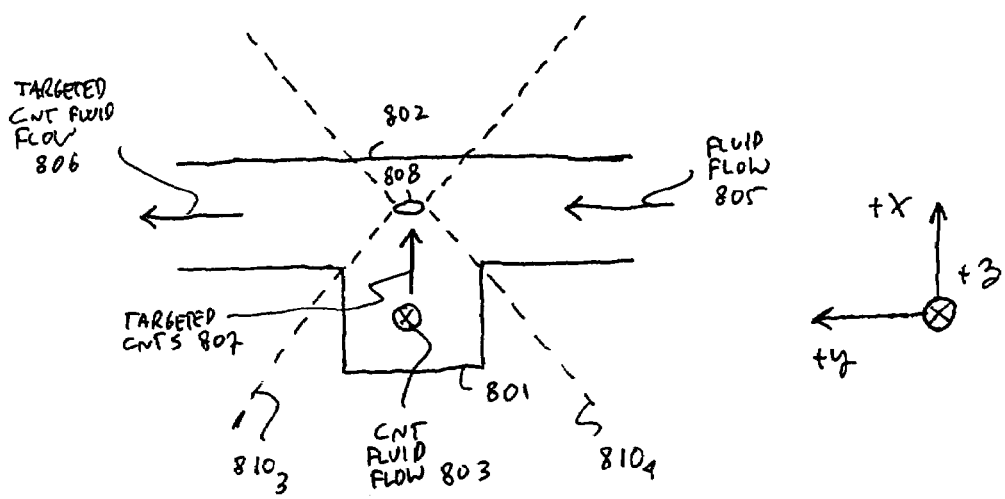

A potential implementation issue with the approach of FIGS. 8a-8c is the optics. That is, assuming channel 801 is truly "beneath" channel 802, the light 809 is focused along the side of the chip/carrier that the channels 801, 802 are constructed in. FIGS. 8d and 8e show another approach that is perhaps easier to implement that the approach of FIGS. 8a-8c if channel 802 is higher along the vertical axis than channel 801. According to the approach of FIGS. 8d and 8e, the applied light 810 will travel along the vertical axis if channels 801, and 802 run along different vertical planes.

The behavior of the various flows 803 through 807 are the same as described with respect to FIGS. 8a through 8c. Note that according to the depictions of FIGS. 8d and 8e, the electrical component of the applied light 810 will have a frequency beneath the resonant frequency of the targeted CNTs to attract them "up" into channel 802. In an alternate approach, the focal point 808 of the light can be lowered to the bottom of channel 801 (or beneath channel 801) and the frequency of the electrical component of the light can be set above the resonant frequency of the targeted CNTs. This will cause the targeted CNTs to be repelled "up" into channel.

Figure 8F:
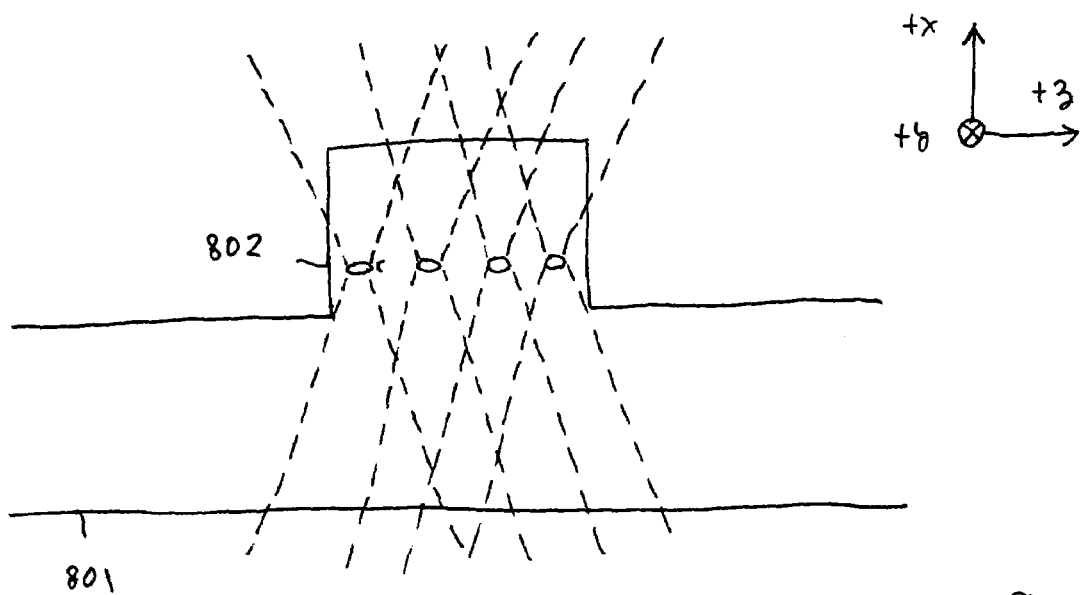

FIG. 8f shows an elaboration on the technique of FIGS. 8d and 8e. Here, multiple beams of light are depicted as being applied through the intersection of channels 801 and 802. Similar to the discussion provided above with respect to FIG. 4, multiple beams of light can improve the collection efficiency by applying stronger electric field intensity gradients and/or applying light to a channel region that might receive little or no light with a single applied beam of light. According to the depiction of FIG. 8f, focal points of the various beams are found along the z axis. Similarly, although not shown, focal points of other additional beams may be found along the y axis. Also, and again not depicted in FIG. 8f, the focal points may be positioned at different x axis levels to form the collection light appropriately. Multiple beams of light may be applied to the collection approach described in FIGS. 8a through 8c as well as the collection approach of FIGS. 8d and 8e as just described. Finally, the beams of light may be positioned to attract or repel targeted CNTs based upon the position of the focal points.

For any of the approaches described above note that if the laser power is high it will produce strong attraction/repulsion forces which corresponds to a strong optical force. Generally, in order to provide the strongest sorting affect, it is advisable to maintain the flow rate at a level that causes the drag forces created by the flow to be smaller than the optical attraction/repulsion forces. In terms of the useable solution(s) for implementing the fluid flows, water or any solution that solubilizes CNTs may be used (water, organic solvents, acids, etc.) provided that the solution does not destroy the fluidic channel.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

The invention claimed is:

1. A method, comprising
sorting carbon nanotubes (CNTs) within a fluidic flow for a targeted subset of said CNTs, said sorting comprising
attracting at least a portion of said CNTs within said fluidic flow in a direction of increasing intensity of an electric field component of substantially stationary beam of light, said electric field component having a frequency that is less than one or more resonant frequencies of said CNTs within said portion; and
attracting a second portion of said CNTs in a direction of increasing intensity of an electric field component of a substantially stationary second beam of light, said electric field component of said second beam of light having a frequency that is less than one or more resonant frequencies of said CNTs within said second portion, said second portion from those of said CNTs within said fluidic flow that were repelled in a direction of decreasing intensity of said electric field component of said beam of light.

2. The method of claim 1 wherein said portion comprises said targeted subset.

3. The method of claim 1 wherein said substantially stationary beam of light further comprises a substantially stationary beam of laser light.

4. The method of claim 3 wherein said stationary beam of laser light is focused to a spot within said fluidic flow.

5. The method of claim 4 wherein said CNTs are made to substantially flow: along or off to a side of said spot and not along or off to another side of said spot that is opposite of said side.

6. The method of claim 5 wherein said attracting draws said portion of said CNTs from said fluidic flow into another fluidic flow.

7. The method of claim 6 wherein said portion comprises said targeted subset.

8. The method of claim 6 wherein said beam of light is one of multiple beams of light each of whose electric field component is less than said one or more resonant frequencies.

9. The method of claim 1 wherein said electronic component of said second beam of light has a second frequency that is less than said frequency.

10. The method of claim 1 wherein said electronic component of said second beam of light has a second frequency that is greater than said frequency.

11. The method of claim 1 wherein said electronic component of said beam of light has a second frequency that is less than said one or more resonant frequencies.

12. The method of claim 1 further comprising said targeted subset of CNTs moving into a second fluidic flow that runs along a different vertical plane that said fluidic flow.

* * * * *